(12) United States Patent
Cahan

(10) Patent No.: US 10,441,502 B2
(45) Date of Patent: Oct. 15, 2019

(54) ACOUSTIC STIMULATION FOR THE PREVENTION AND TREATMENT OF OBESITY

(71) Applicant: International Business Machines Corporation, Armonk, NY (US)

(72) Inventor: Amos Cahan, Dobbs Ferry, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 376 days.

(21) Appl. No.: 14/744,150

(22) Filed: Jun. 19, 2015

(65) Prior Publication Data

US 2016/0310305 A1   Oct. 27, 2016

Related U.S. Application Data

(63) Continuation of application No. 14/696,706, filed on Apr. 27, 2015.

(51) Int. Cl.
*A61H 23/02* (2006.01)
*A61N 7/00* (2006.01)
*A61F 5/00* (2006.01)

(52) U.S. Cl.
CPC ....... *A61H 23/0236* (2013.01); *A61F 5/0003* (2013.01); *A61N 7/00* (2013.01); *A61H 2201/0111* (2013.01); *A61H 2201/1207* (2013.01); *A61H 2201/16* (2013.01); *A61H 2203/02* (2013.01); *A61H 2205/083* (2013.01)

(58) Field of Classification Search
None
See application file for complete search history.

(56) References Cited

U.S. PATENT DOCUMENTS

| | | | | |
|---|---|---|---|---|
| 5,188,104 A | * | 2/1993 | Wernicke | A61N 1/36007 607/40 |
| 6,587,719 B1 | * | 7/2003 | Barrett | A61N 1/05 607/2 |
| 6,595,928 B2 | * | 7/2003 | Mansy | A61B 8/08 600/529 |
| 8,818,502 B2 | * | 8/2014 | Schuler | A61N 1/326 600/545 |
| 2006/0276729 A1 | * | 12/2006 | Reed | A61H 23/0263 601/46 |
| 2008/0294010 A1 | * | 11/2008 | Cooper | A61B 1/267 600/199 |

(Continued)

OTHER PUBLICATIONS

"Infrasound, Brief review of toxicological literature". Infrasound Toxicological Summary, Nov. 2001.*

(Continued)

*Primary Examiner* — Amelie R Gillman
*Assistant Examiner* — Yi-Shan Yang
(74) *Attorney, Agent, or Firm* — Cantor Colburn LLP; Kristofer Haggerty

(57) ABSTRACT

A method for inducing a cellular or hormonal response includes using a wave-generating device to emit sound waves through an individual's skin and onto a target organ, and vibrating the target organ or a portion thereof at a frequency in resonance with the sound waves. The sound waves have a frequency of less than 200 Megahertz (MHz).

7 Claims, 2 Drawing Sheets

(56) References Cited

U.S. PATENT DOCUMENTS

| | | | |
|---|---|---|---|
| 2010/0179458 A1* | 7/2010 | Venturi | A61H 23/0236 601/47 |
| 2011/0006901 A1* | 1/2011 | Cassidy | A61B 5/14551 340/573.1 |
| 2011/0130625 A1* | 6/2011 | Lior | A61F 5/003 600/37 |
| 2013/0046150 A1* | 2/2013 | Devanaboyina | A61B 5/0024 600/301 |
| 2013/0281897 A1* | 10/2013 | Hoffmann | A61B 8/08 601/107 |
| 2014/0369514 A1* | 12/2014 | Baym | G10K 11/178 381/71.1 |
| 2016/0001096 A1* | 1/2016 | Mishelevich | A61N 7/00 601/2 |
| 2016/0121062 A1* | 5/2016 | Davenport | A61B 5/097 601/47 |
| 2016/0151238 A1* | 6/2016 | Crunick | A61H 23/0218 601/2 |
| 2016/0161595 A1* | 6/2016 | Benattar | G01S 5/26 367/117 |

OTHER PUBLICATIONS

Amos Cahan; "Acoustic Stimulation for the Prevention and Treatment of Obesity"; U.S. Appl. No. 14/696,706, filed Apr. 27, 2015.
List of IBM Patents or Patent Applications Treated as Related—Date Filed: Aug. 17, 2015; 1 page.

\* cited by examiner

ACOUSTIC STIMULATION FOR THE PREVENTION AND TREATMENT OF OBESITY

PRIORITY

This application is a continuation of and claims priority from U.S. patent application Ser. No. 14/696,706, filed on Apr. 27, 2015, entitled "ACOUSTIC STIMULATION FOR THE PREVENTION AND TREATMENT OF OBESITY", the entire contents of which are incorporated herein by reference.

BACKGROUND

The present disclosure generally relates to methods for inducing cellular or hormonal changes, and more specifically, to methods using sound waves for inducing cellular or hormonal changes.

Obesity is a pandemic. Over the last decade, the prevalence of diabetes has followed the obesity trend. Currently, the cost of providing medical care and treatment to obese and diabetic patients is costly, at more than $100 billion per year. Medical treatment includes physician and hospital costs, insurance (both private insurance and government subsidized), and pharmaceutical research and development.

A variety of obesity treatments exist. However, noninvasive treatments, such as medications, can generally only induce less than a 10% reduction in weight. Thus, these noninvasive treatments have largely failed. While invasive treatments, such as bariatric surgery, are more effective in inducing a substantially greater weight loss, they are nonetheless risky and costly.

Some minimally invasive treatment options control appetite. Enhancing satiety results in reduced food consumption and weight loss. Procedures to induce gastric distention, or to prevent gastric emptying, induce satiety. When gastric emptying is prevented, isotonic saline is comparable to a liquid diet in reducing desire for food intake. Balloons used to induce gastric distention can induce feelings of satiety and satiety-related brain activation. These treatments indicate that satiety may be induced by mechanical stimuli.

Hormones are involved in weight regulation. Various hormones, for example, leptin, gherlin, cholecystokinin (CCK), and pancreatic peptide YY3-36 (PYY3-36), regulate food intake by interacting with or binding to mechanoreceptors dispersed along the gastrointestinal tract.

Vagus nerve stimulation (VNS) is an invasive treatment for satiety induction. VNS therapy, which originally was an epileptic treatment, involves implanting electrodes to electrically stimulate various regions of the brain. Although animal studies demonstrate decreased food intake and weight loss, human studies may demonstrate less favorable results. Human studies provide contradictory reports in retrospective analysis of epilepsy patients.

Gastric pacing is another invasive intervention for inducing satiety. A gastric pacemaker is implanted under the skin to deliver electrical stimulation to the stomach. The pacemaker senses naturally-occurring electrical activity of the stomach and automatically applies electrical stimulation treatment during meal times. The stimulation during initial stages of meals is designed to provoke an early response of the gut typical of a full meal.

SUMMARY

In one embodiment of the present disclosure, a method for inducing a cellular or hormonal response includes using a wave-generating device to emit sound waves through an individual's skin and onto a target organ, and vibrating the target organ or a portion thereof at a frequency in resonance with the sound waves. The sound waves have a frequency of less than 200 Megahertz (MHz).

In another embodiment, a method for inducing a cellular or hormonal response includes using a wave-generating device to emit sound waves through an individual's skin and onto a target organ, and vibrating the target organ at a frequency in resonance with the sound waves. The sound waves have a frequency of less than 20,000 Hz.

Yet, in another embodiment, a device for inducing a cellular or hormonal response includes an infrasound wave generator, a power supply connected to the infrasound wave generator, a power control connected to the power supply, and an infrasound wave emitting portion operative to transmit infrasound waves through an individual's skin and onto an organ of interest.

BRIEF DESCRIPTION OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

Figure 1:
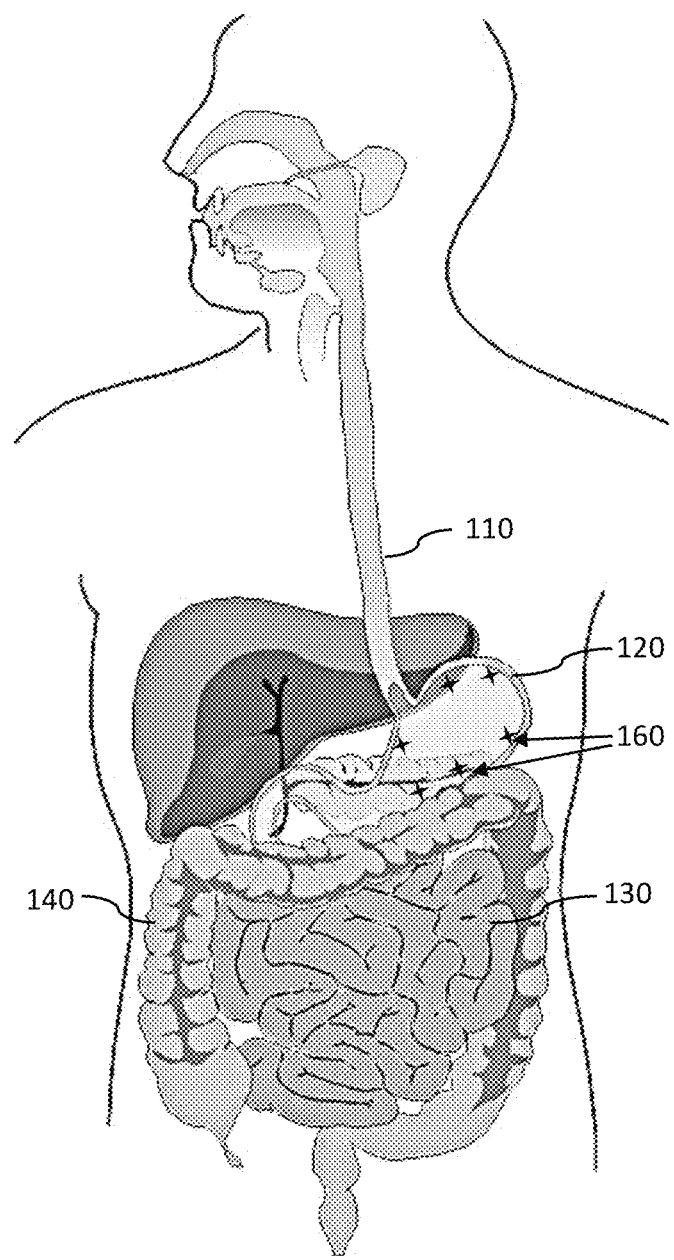
FIG. 1 illustrates a schematic diagram of exemplary organs in a gastrointestinal tract.

The present disclosure relates to non-invasive methods and devices for inducing a cellular or hormonal response. The methods and devices use sound waves to induce vibration of gastrointestinal organs, and other organs, in resonance with the frequency of the sound waves. The methods and devices stimulate or trigger mechanoreceptors lining the organs of the gastrointestinal tract. The methods and devices also can be used to stimulate glands or hormone secreting cells to produce hormones or to down-regulate production or release of hormones. Non-limiting examples of hormones include leptin, gherlin, cholecystokinin (CCK), and pancreatic peptide YY3-36 (PYY3-36), or any combination thereof. The hormones may regulate food intake by affecting the brain and by interacting with or binding to adjunct cells. The methods and devices can be used to treat or prevent obesity.

The present disclosure is now described in detail with accompanying figures. It is noted that like reference numerals refer to like elements across different embodiments.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

As used herein, the articles "a" and "an" preceding an element or component are intended to be nonrestrictive regarding the number of instances (i.e. occurrences) of the element or component. Therefore, "a" or "an" should be read to include one or at least one, and the singular word form of the element or component also includes the plural unless the number is obviously meant to be singular.

As used herein, the terms "invention" or "present invention" are non-limiting terms and not intended to refer to any single aspect of the particular invention but encompass all possible aspects as described in the specification and the claims.

As used herein, the term "about" modifying the quantity of an ingredient, component, or reactant of the invention employed refers to variation in the numerical quantity that can occur, for example, through typical measuring and liquid handling procedures used for making concentrates or solutions. Furthermore, variation can occur from inadvertent error in measuring procedures, differences in the manufacture, source, or purity of the ingredients employed to make the compositions or carry out the methods, and the like. In one aspect, the term "about" means within 10% of the reported numerical value. In another aspect, the term "about" means within 5% of the reported numerical value. Yet, in another aspect, the term "about" means within 10, 9, 8, 7, 6, 5, 4, 3, 2, or 1% of the reported numerical value.

FIG. 1 illustrates a schematic diagram of a gastrointestinal tract, which includes various exemplary organs that can be targeted and stimulated by sound waves. Cellular or hormonal responses are induced indirectly by using a wave-generating device to emit sound waves through an individual's skin and onto a target organ. The target organ can be an organ within the gastrointestinal tract, for example, the esophagus 110, the stomach 120, the small intestine 130, the large intestine 140, or any combination thereof. Substantially the entire organ or a portion of the target organ stimulated. The individual can be a human or an animal.

Sounds waves may be generated using any known technology or device, including but not limited to, a loudspeaker, a horn, a whistle, a vibrating device, or any combination thereof.

Depending on the form and shape of the sound wave generating device, the sound waves travel through any medium. The sound waves can travel through the surrounding gas, for example air. The sound waves can travel through liquid, for example water. The sound waves travel through the individual's skin, surrounding tissues, and induce vibration of the target organ at a frequency in resonance with the sound waves.

The sound waves can be infrasound waves, acoustic sound waves, ultrasound waves, or any combination thereof. Infrasound waves have a low frequency, for example, less than 20 Hertz (Hz), or cycles per second. In one embodiment, the infrasound waves have a frequency in a range from about 0.001 to about 20 Hz. In some embodiments, the infrasound waves have a frequency about or in any range from about 0.001, 1, 2, 3, 4, 5, 6, 7, 8, 9, 10, 11, 12, 13, 14, 15, 16, 17, 18, 19, and 20 Hz.

Acoustic sound waves have a frequency, for example, in a range from about 20 to about 20,000 Hz (20 kHz). In some embodiments, acoustic sound waves have a frequency about or in any range from about 20, 1,000, 3,000, 5,000, 7,000, 10,000, 13,000, 15,000, 17,000, and 20,000 Hz.

Ultrasound waves have a frequency, for example, of greater than 20 kHz. In other embodiments, ultrasound waves have a frequency about or in any range from about 20 kHz, 1,000 kHz (1 MHz), 2 MHz, 50 MHz, 100 MHz, 150 MHz, and 200 MHz.

The sound waves vibrate or oscillate the organ(s) of interest. Substantially the entire organ or a portion of the organ may vibrate or oscillate. For example, just a portion of the organ's tissue may vibrate or oscillate.

The vibrations occur at a frequency in resonance with the sound waves. The organs will therefore resonate at the frequencies of the sound waves disclosed above.

The vibrations are macroscopic or microscopic organ or tissue excitations, which then indirectly induce other cellular or hormonal changes. The vibrations can indirectly induce neural stimulation, for example stimulation of the vagus nerve. Vagus nerve stimulation can induce a feeling of fullness or satiety.

The organ vibrations can indirectly induce formation and/or secretion of hormones or other neuroendocrine metabolites. These changes may induce satiety or reduce appetite, which can result in weight loss.

The organ vibrations can also signal stomach distention or fullness in the individual. These methods also can be used to treat or prevent obesity or control weight loss.

The organ vibrations can induce mechanical excitation or displacement of cell membranes or of microscopic or macroscopic structures within or adjacent to the organ's wall.

In another embodiment, the organ vibrations may cause inhibition of formation or secretion of hormones, metabolites, or mediators that increase or affect appetite. Thus, these changes reduce appetite and decrease food intake.

In one embodiment, the organ of interest is a targeted secretary organ. The target secretary organ can be, for example, a gland, a hormone secreting cell, or both. Excitation of secretary glands can then alter or adjust hormone secretion or enzyme secretion to induce downstream changes, for example other cellular or hormonal changes. Non-limiting examples of target secretary organs include a salivary gland, a lacrimal gland, a biliary gland, a mucus gland, a sweat gland, a sebaceous gland, a pancreas, or any combination thereof.

Excitation of salivary glands can increase saliva production. A sound wave generating device is placed on or in proximity to the skin overlying a salivary organ to induce stimulation. The methods and devices can be used to treat various salivary gland conditions, for example, sicca syndrome and dry mouth.

Excitation of lacrimal glands can be induced. Lacrimal glands can be induced to increase tear formation.

Excitation of biliary glands can be induced. Exciting biliary glands can prevent biliary stasis. Exciting biliary glands can treat biliary stones or prevent their formation.

Excitation of the endocrine pancreas can be induced. The excited endocrine pancreas can induce insulin secretion in individuals with delayed post-prandial insulin secretion, for example, those with impaired glucose tolerance.

Excitation of the exocrine pancreas can be induced. The excited exocrine pancreas can then release enzymes, compounds, and metabolites that play a role in food digestion.

Excitation of the small intestine, the large intestine, or both, can be induced. The excited small and/or large intestines can induce peristalsis to prevent or treat constipation or diarrhea.

Excitation of the esophagus can be induced. The esophageal excitation can be used, for example, to treat or prevent reflux.

Excitation of the stomach can be induced. The method can be used to treat, for example, gastroparesis.

The sound waves can generally excite various organs and tissues in the gastrointestinal tract. The excitations can change the composition and/or the function of the gastrointestinal tract or gut microbiota. The excitations can change the gut's microbiota interaction with intestinal mucosa.

The sound waves activate or stimulate mechanoreceptors 160 lining the organ of interest. Stimulation of the mechanoreceptors 160 can then indirectly induce any of the above described cellular or hormonal changes. For example, stimulating the mechanoreceptors 160 can indirectly induce satiety, or a feeling of fullness.

In one embodiment, the sound waves can activate or stimulate nerve cells. The nerve cells can line the target organ.

Figure 2:
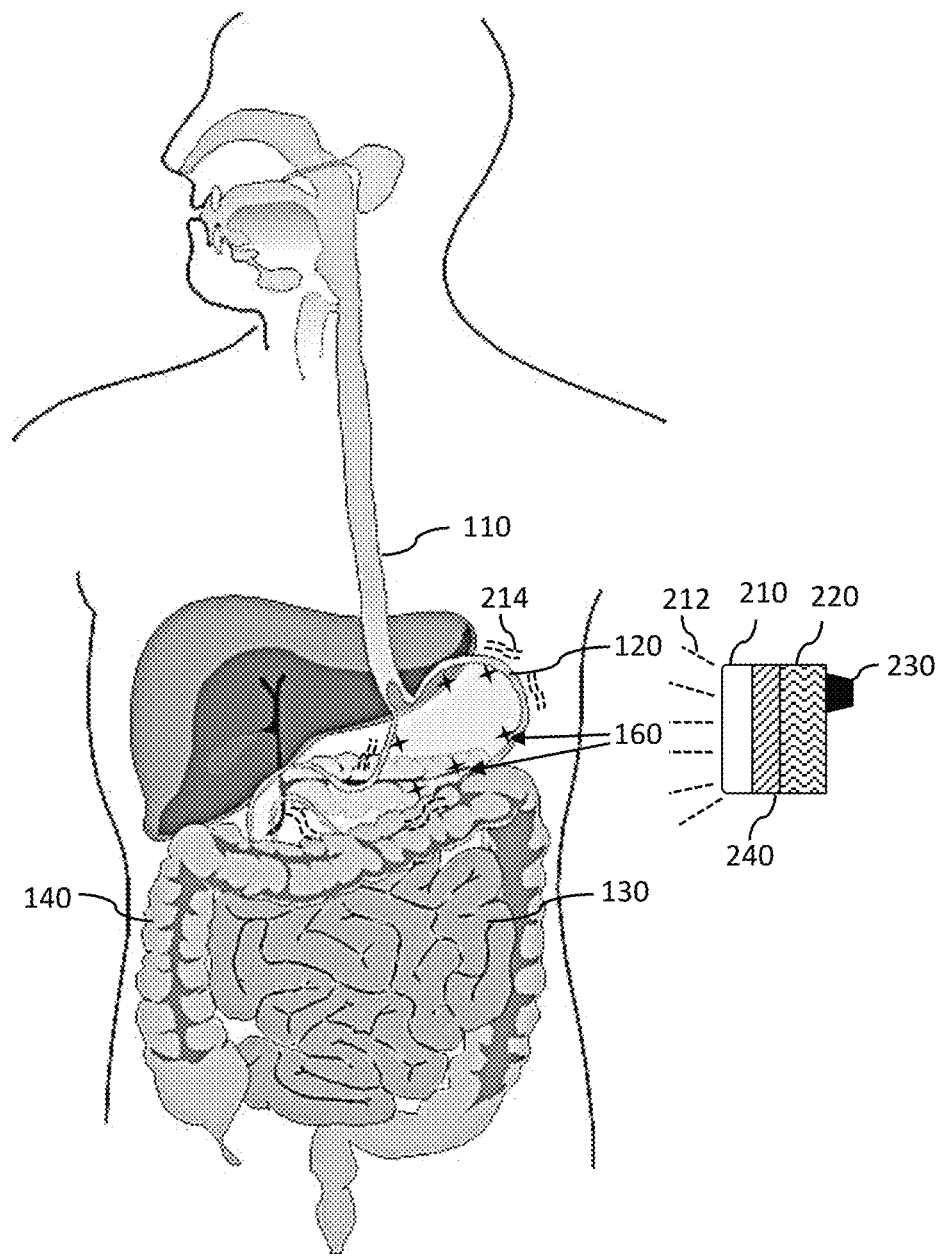
FIG. 2 illustrates a schematic diagram of transmitting sound waves to induce vibration of an organ of interest in the gastrointestinal tract.

FIG. 2 illustrates a schematic diagram of a device for inducing cellular or hormonal changes according to an exemplary embodiment. The device includes an infrasound wave generator 240, a power supply 220 connected to the infrasound wave generator 240, a power control 230 connected to the power supply 220, and an infrasound wave emitting portion 210 operative to transmit infrasound waves 212 through an individual's skin and onto an organ of interest. The organ of interest vibrates 214 in resonance with the infrasound waves 212. The power control 230 can be connected to the power supply 220, for example, by a wire (not shown).

In other embodiment, the power control 230 also can be connected to the power supply 220 by a wireless means, or the power control 230 can be separate unit from the power supply (not shown). The power control 230 can be a computer, a smart phone, or other device adjusted to control the infrasound wave generator using hardware or software.

The device may be used in the setting of the individual's home or office. The device may be used when in motion, for example, when in a car or while performing physical exercise. The device can be handheld, stationary, or affixed to the body by physical means, such as by a strap. The device can be made available through service providers, for example, beauty salons and clinics.

The infrasound wave emitting portion 210 can include a skin contacting portion. The infrasound wave emitting portion 210 can provide one or more focused infrasound wave beams that will not stimulate or affect other organs. The device may include a means for modifying (e.g., increasing or decreasing) the infrasound wave beam signal amplitude and/or energy. The infrasound wave emitting portion 210 is operative to transmit the infrasound waves 212 through any medium, for example, air or water.

The device can emit sound waves at fixed frequencies. Or, the device can emit sound waves as a combination of frequencies.

The device can be in any form. The device can be a handheld device. The device can be, for example, a belt that the individual wears underneath or on top of clothing. Because the sound waves can travel through any medium, for example water, the device can be used in the bath or shower.

The device can include a feedback sensor for monitoring vibrations of the organ of interest and adjusting or altering excitatory output of the device accordingly. The device can include any other mechanism to generate gastric and/or intestinal resonance oscillation or vibration.

The device can be used intermittently. For example, the device can be used before a meal, during a meal, or between meals. In another example, the device can be used during exercising or another activity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method for inducing a cellular or hormonal response to treat obesity, the method comprising:
   using a handheld wave-generating device to transmit infrasound waves through air and through an individual's skin and onto an organ in a gastrointestinal tract, the handheld wave-generating device comprising
     an infrasound wave generator,
     a power supply, a power control, and
     an infrasound wave emitting portion, and
     the handheld wave-generating device being a handheld device in its entirety;
   vibrating the organ or a portion thereof at a frequency in resonance with the infrasound waves; and
   inducing satiety in the individual by vibrating the organ to treat obesity;
     wherein the infrasound waves have a frequency of about 0.001 Hertz (Hz).

2. The method of claim 1, wherein the individual is a human.

3. The method of claim 1, wherein the wave-generating device contacts the individual's skin.

4. The method of claim 1, wherein the wave-generating device emits the infrasound waves through a liquid and then through the individual's skin.

5. The method of claim 1, further comprising activating mechanoreceptors, nerve cells, or a combination thereof, lining the target organ.

6. The method of claim 1, further comprising indirectly stimulating a vagus nerve after vibrating the organ.

7. A method for inducing a cellular or hormonal response, the method comprising:
- using a handheld wave-generating device to transmit infrasound waves through air and through an individual's skin and onto an organ in a gastrointestinal tract, the handheld wave-generating device comprising
  - an infrasound wave generator,
  - a power supply, a power control, and
  - an infrasound wave emitting portion, and
  - the handheld wave-generating device being a handheld device in its entirety;
- vibrating the organ at a frequency in resonance with the infrasound waves; and
- signaling fullness in the individual by vibrating the organ to treat obesity;
  - wherein the infrasound waves have a frequency of about 0.001 Hertz (Hz).

\* \* \* \* \*